Figure 5:
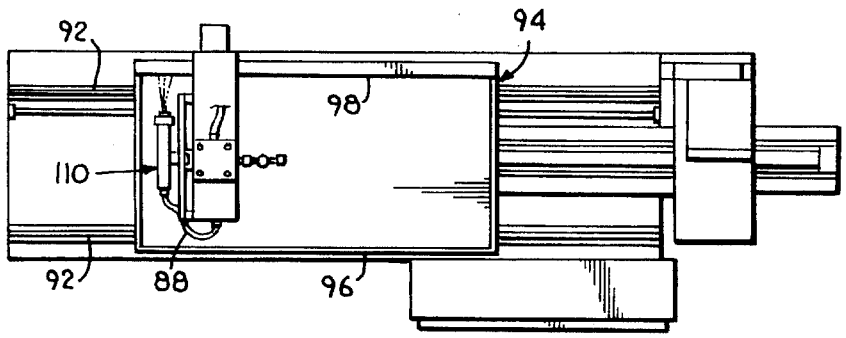

United States Patent [19]

McLaughlin

[11] Patent Number: 5,526,680
[45] Date of Patent: Jun. 18, 1996

[54] HYDRAULIC PRESS FLOW VISCOMETER

[75] Inventor: David E. McLaughlin, Ray, Mich.

[73] Assignee: H. B. Fuller Automotive Technology Systems, Inc., Topeka, Kans.

[21] Appl. No.: 281,067

[22] Filed: Jul. 27, 1994

[51] Int. Cl.$^6$ ................................................ G01N 11/04
[52] U.S. Cl. ........................ 73/54.01; 73/861.49; 73/866
[58] Field of Search ............................ 73/54.01, 54.11, 73/861.61, 861.49, 866, 3, 865.9, 864.62, 864.61, 864.83

[56] References Cited

U.S. PATENT DOCUMENTS

| | | | |
|---|---|---|---|
| 1,925,833 | 9/1933 | French | 73/54.01 |
| 2,038,622 | 4/1936 | Yeager | 73/54.01 |
| 3,677,069 | 7/1972 | Rubin et al. | 73/56 |
| 4,491,023 | 1/1985 | Graef | 73/861 |
| 4,501,143 | 2/1985 | Prior et al. | 73/153 |
| 4,586,386 | 5/1986 | Hollstein et al. | 73/861.04 |
| 4,680,519 | 7/1987 | Chand et al. | 318/568 |
| 4,817,445 | 4/1989 | Fink | 73/864.62 |
| 4,882,930 | 11/1989 | Nagy et al. | 73/56 |
| 4,922,764 | 5/1990 | Welker | 73/864.62 |
| 4,959,995 | 10/1990 | Deysarkar et al. | 73/54 |
| 5,088,335 | 2/1992 | LaFreniere et al. | 73/864.62 |
| 5,226,331 | 7/1993 | Thompson et al. | 73/865.9 |
| 5,410,909 | 5/1995 | Gohara et al. | 73/198 |

Primary Examiner—Hezron E. Williams
Assistant Examiner—J. David Wiggins
Attorney, Agent, or Firm—Shook, Hardy & Bacon

[57] ABSTRACT

A hydraulic press flow viscometer is provided for spray testing viscous materials for high pressure applications using a relatively small sample size. A hydraulic press forces the sample from its container to a spray assembly. The spray testing system is capable of accurately simulating robotic applications in assembly plants by controlling material temperature, material pressure and robot speed. A method is also provided for performing high pressure spray tests on material samples using the hydraulic spray testing system.

18 Claims, 4 Drawing Sheets

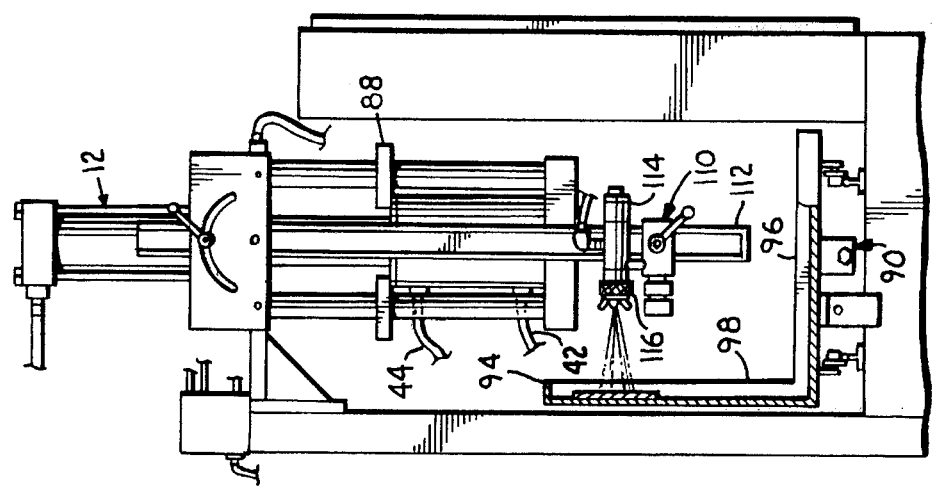
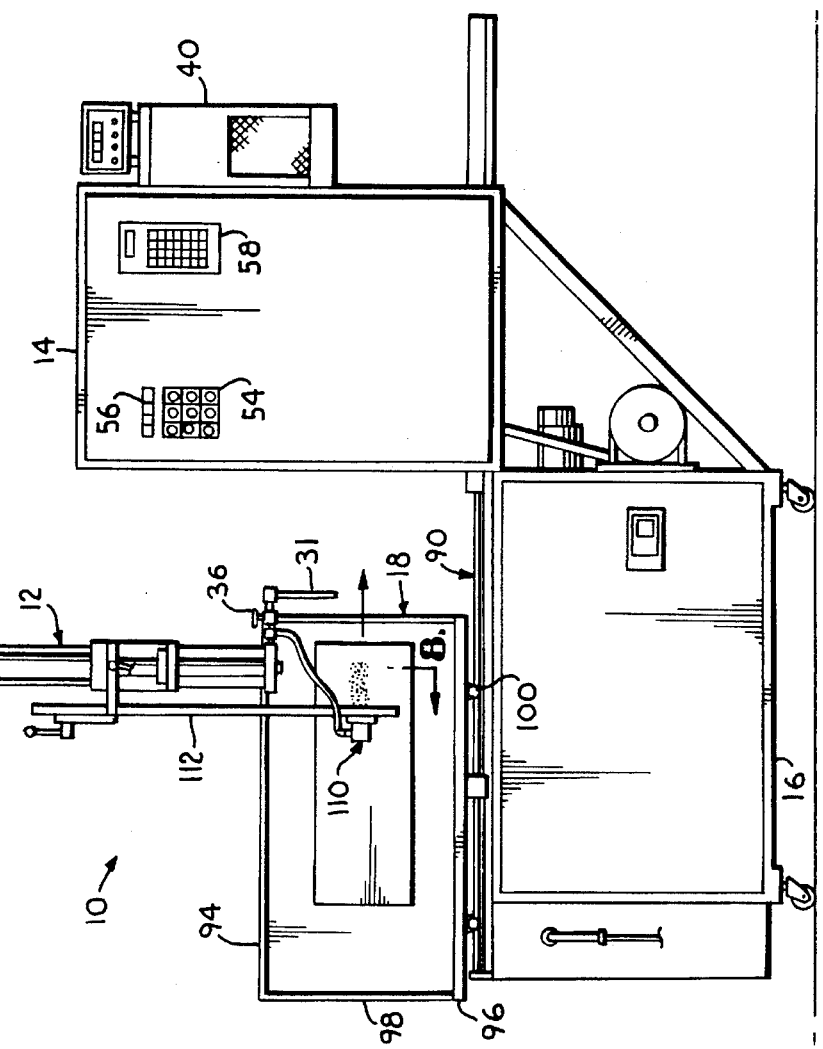

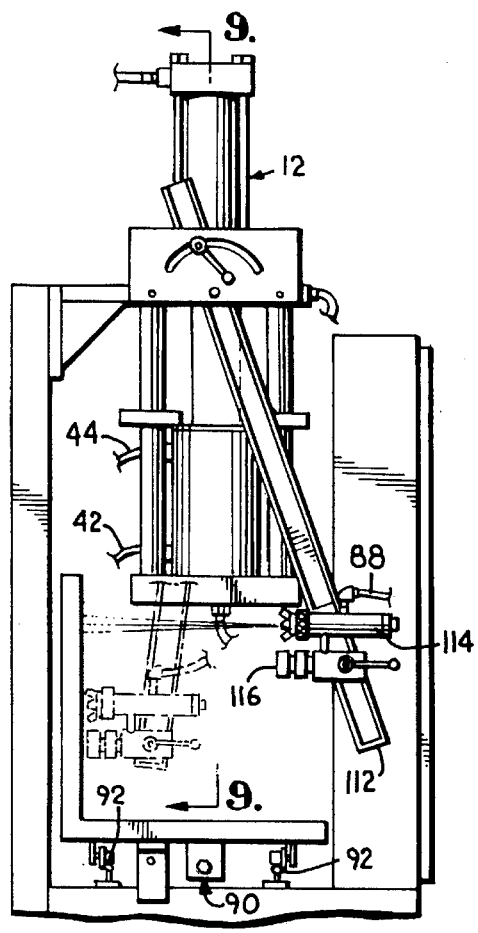
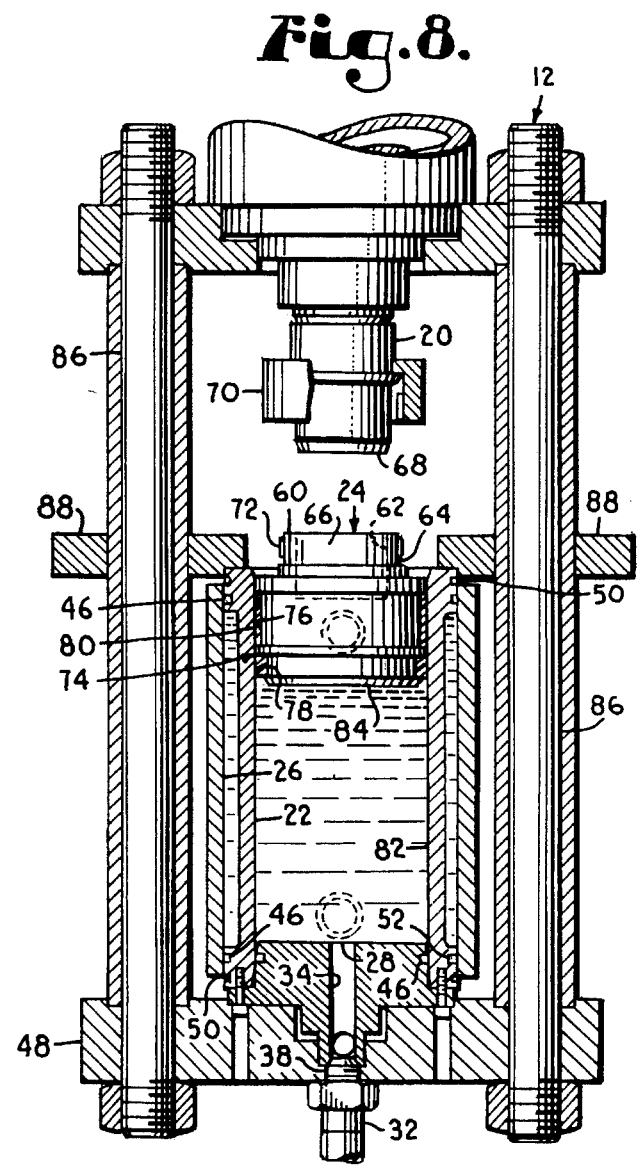
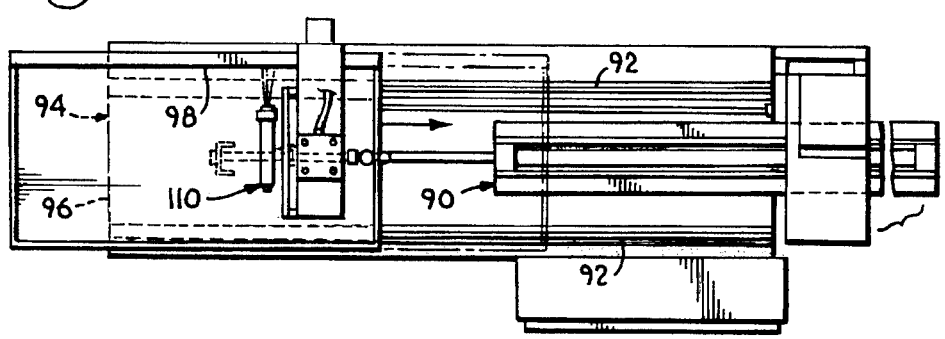

HYDRAULIC PRESS FLOW VISCOMETER

BACKGROUND OF THE INVENTION

This invention relates in general to spray equipment for testing the performance of viscous materials for high pressure spray applications and, more particularly, to hydraulic spray equipment capable of reducing the sample size required for testing purposes while more accurately testing such materials by precisely simulating assembly plant conditions.

The standard method of testing the "sprayability" of viscous materials, such as polyvinylchloride sealants or polyurethanes, involves the use of high pressure airless spray equipment. Such equipment, however, generally requires that at least a five gallon sample of material be prepared in order to conduct the necessary testing. A significant portion of the material sample is also wasted during the purging which is required to clean the hoses and other components of the system. Because tens and sometimes hundreds of experimental samples must be tested when a new product is being developed, the large quantities of material samples which must be prepared add significantly to the product development costs and can create environmental disposal issues as well.

Another problem with the use of conventional high pressure airless spray equipment is the temperature, pressure and speed controls provided in these systems often lack the precision necessary to provide reliable test data. Maintaining the desired sample temperature is particularly problematic because even if the sample is provided at the desired temperature, it might travel ten to twenty feet through material lines before reaching the spray valve. Additionally, the system must be purged before the sample is tested. Thus, the temperature of the sample may change before it is actually tested. Although it is possible to control the temperature of the entire room containing the spray equipment, such an approach is costly and time consuming, particularly in those situations where material samples are tested by gathering data points at ten degree increments, such as between 50° F. and 100° F.

Temperature control can be improved somewhat in airless systems by providing a heat exchanger. However, adding such a component to the system would substantially increase the minimum sample size and the time required for sample testing. Likewise, it is generally undesirable to provide robots for speed control in standard airless systems because it would increase the required sample size.

Pressure control with standard airless equipment is also unsatisfactory. A pressure gauge on a conventional spray gun will indicate that actual spray pressure varies significantly over time. While this variance may eventually even out, it can significantly alter the results of a test to measure spray pattern width. Even for flow rate testing the results may not be very accurate unless a substantial amount of material is used.

Although low pressure testing might adequately test most fresh material samples, it is unacceptable as a testing method for aged materials. In particular, low pressure testing of aged materials fails to accurately predict such critical parameters as spray pattern width and spray delivery rate. Furthermore, test results from low pressure testing will not necessarily predict spray performance for high pressure applications.

Moreover, there is a need for spray equipment capable of accurately testing the sprayability of both fresh and aged materials for high pressure applications. Conventional spray testing equipment maintains relatively imprecise temperature and pressure control for the sample material and provides no robot speed control for the spraying action. Furthermore, a problem exists with conventional testing equipment in that a relatively large quantity of material, typically at least five gallons, is required as a sample in order to test for such important parameters as spray pattern width and spray delivery rate. Additionally, at least two of these five gallons of material are wasted purging a conventional system. Consequently, substantial amounts of time, storage space, and material are unnecessarily consumed to prepare, store, and test the samples.

SUMMARY OF THE INVENTION

The present invention overcomes the problems encountered with conventional test equipment. The spray testing system of the present invention requires a very small sample size, only about one quart of material, and comprehensive testing can be completed in less than one hour. Thus, important resources such as time, storage space, and the amount of prepared and wasted material are significantly conserved. Moreover, by using these resources more efficiently, the present invention significantly reduces the costs associated with researching and developing products.

Further, the present invention utilizes a programmable linear motion system to simulate robotic applications. More particularly, a test panel may be moved linearly in proximity to a spray assembly to generate the type of movement found in an assembly plant. The speed at which the test panel moves is variable and may be programmed to correspond with a particular application.

The hydraulic press flow viscometer utilizes a hydraulic system for operating the hydraulic press and the linear motion system. The hydraulic press is raised to fill the sample container and lowered to force the sample toward the spray assembly. Then the sample exits the spray assembly through a spray valve in either a fan pattern or a bead pattern. The spray valve may direct the sample toward a target surface or a material recovery cup.

Therefore, the present invention is capable of completely simulating assembly plant conditions by precisely controlling material temperature, material pressure, and robot speed. Importantly, the present invention requires only a one quart sample of material to conduct comprehensive spray testing that fully simulates assembly plant conditions.

Accordingly, it is a primary object of the present invention to provide a system having a hydraulic press for spray testing viscous materials that provides precise temperature, pressure and speed control yet requires a reduced sample size.

Another object of the present invention is to provide a system for spray testing viscous materials that is capable of comprehensively testing a material sample in an hour or less.

A further object of the present invention is to provide a system for spray testing viscous materials that is capable of obtaining accurate results for both fresh and aged materials.

Yet another object of the present invention is to provide a programmable linear motion system so that robotic applications in assembly plants may be simulated with greater accuracy.

Still another object of the present invention is to provide a system for spray testing viscous materials that is substantially self-cleaning.

Still a further object of the present invention is to provide a method for spray testing viscous materials to more precisely predict the actual spray pattern characteristics of the material.

It is a further object of the present invention to provide a method for spray testing viscous materials to more precisely predict the actual spray delivery characteristics of the material.

Yet another object of the present invention is to provide a method for spray testing viscous materials by simulating practical robotic applications.

These and other objects of the present invention will become readily apparent upon further review of the following specification and drawings. To accomplish these and other objects of the present invention, a system and method are provided for testing the spray characteristics of viscous materials for high pressure applications wherein a hydraulic press forces a material sample out of a cylindrical cup and toward a spray assembly where it is then dispersed through a spray tip. The temperature and pressure of the sample material are maintained at selected values, and a programmable linear motion system is provided to maintain the desired robot speed.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a front elevation view of an apparatus constructed in accordance with the present invention and including a hydraulic press flow viscometer for extruding high viscosity materials at high pressures;

FIG. 2 is a fragmentary end elevation view of the apparatus shown in FIG. 1 and illustrating the use of the hydraulic press flow viscometer to spray a vertically-oriented test panel;

FIG. 3 is an end elevation view of the apparatus and similar to the view shown in FIG. 2 but with the spray assembly of the flow viscometer being moved further from the slide tray and with phantom lines being used to illustrate positioning of the spray assembly more closely to the slide tray;

FIG. 4 is a top plan view of the apparatus shown in FIG. 1 with broken lines to illustrate movement of the slide tray, which moves the test panels back and forth in relation to the flow viscometer spray assembly and is shown at one end of its path of travel, the programmable linear motion system includes a cylinder which effects the reciprocating movement of the slide tray and is shown in fragment;

FIG. 5 is a top plan view of the apparatus and similar to the view shown in FIG. 4 but with the slide tray being reciprocated to the other end of its path of travel;

FIG. 6 is a fragmentary end elevation view of the apparatus and similar to the view shown in FIG. 2 but with the spray assembly being repositioned to spray a horizontally-oriented test panel;

FIG. 7 is a fragmentary front elevation view of the slide tray and the tracks along which it is movable, the view taken in vertical section along line 7—7 of FIG. 6 in the direction of the arrows;

FIG. 8 is an enlarged end elevation view of the hydraulic press flow viscometer taken in vertical section along line 8—8 of FIG. 1 in the direction of the arrows, portions removed for purposes of illustration;

FIG. 9 is a front elevation view of the hydraulic press flow viscometer taken in vertical section along line 9—9 of FIG. 3 in the direction of the arrows and with portions of the viscometer being shown in fragment; and FIG. 10 is a schematic of the hydraulic system in a preferred embodiment of the hydraulic press flow viscometer of the present invention.

DETAILED DESCRIPTION OF THE PREFERRED EMBODIMENTS

Referring to the drawings in greater detail, and initially to FIGS. 1 and 2, a hydraulic press flow viscometer is designated generally by the numeral 10 and provides an apparatus and method for spray testing a material sample. The system 10 comprises a hydraulic press assembly 12, a control panel 14 which is operatively coupled with the assembly 12, a cabinet 16 in which the assembly is housed, a programmable linear motion system 18, and a spray assembly 110.

The control panel 14 comprises a control pad 54 having an adjacent display 56 and a programmable controller interface 58 on the face of the panel 14. A programmable controller (not shown) corresponding to interface 58 is located behind the control panel 14 along with affiliated controllers and related hardware (not shown). In the preferred embodiment, a 240 volt power supply, such as the Vickers EMRS-A-11, drives the entire system. The programmable controller in the preferred embodiment is a Parker Digital Servo Controller PMC 10T, which also has a 24 volt power supply, the Parker PS24. One skilled in the art might select another commercial controller with similar functionality or might elect to utilize relay logic or some other conventional means of controlling the system. This is contemplated by and is within the scope of the invention.

The cabinet 16 is located below the hydraulic press assembly 12 and provides a base surface for the programmable linear motion system 18. A hydraulic pump and a digital pressure transducer (both shown in FIG. 10) are located within cabinet 16.

As shown in FIGS. 4 and 7, the programmable linear motion system 18 comprises a cylinder piston subassembly 90, a set of tracks 92, and a slide tray 94 having a horizontal surface 96 and a vertical surface 98. The slide tray 94 rests above the cabinet on wheels 100 that move along tracks 92.

Turning to FIGS. 8 and 9, the hydraulic press assembly 12 comprises a hydraulic press 20, an annular sample storage cup 22 with a piston lid 24, and an annular jacket 26. In a preferred embodiment, cup 22 is made of steel and surrounded by an aluminum jacket 26. However, any suitable metal, ceramic, plastic or other material may be used to manufacture cup 22 or jacket 26. Press 20 can be of the type known to those of ordinary skill in the hydraulic press art but the hydraulic press assembly 12 must be customized for use with high pressure spray equipment. For example, the types of seals used, the temperature and pressure ranges, and the flow rates must be selected for the purpose of spray testing viscous materials.

The sample storage cup 22 is removably positioned below press 20. A cooling or heating medium, such as water, may be circulated from a water chiller 40 (shown in FIG. 1) into the annular space between the container and its annular jacket 26. The medium enters the annular space through an inlet 42 in the jacket 26, circulates around the exterior of cup 22, and exits through an outlet 44 in jacket 26. In one embodiment of the present invention, the medium exiting jacket 26 through outlet 44 is routed through a manifold (not shown) before returning to chiller 40. The manifold directs the medium in proximity to a material line within a jacketed flow line 118 (shown in FIGS. 1 and 5).

Cup 22 is maintained in an upright position by a pair of vertical posts 86, a pair of clamp plates 88 and a bottom plate 48. O-ring seals 46 above and below the circulation space between cup 22 and jacket 26 prevent leakage of the medium. The bottom of upright cup 22 rests above bottom plate 48 of assembly 12. Additionally, snap rings 50 at the top and bottom of annular jacket 26 engage notches 52 at the top and bottom of the exterior of cup 22 to hold cup 22 in place.

The cylindrical removable sample cup 22 has a piston lid 24. When the hydraulic press descends onto and engages lid 24, the lid 24 acts like a piston as it is driven down into the sample container. The sample is compressed and forced through an outlet 28 at the bottom of cup 22. Outlet 28 is coupled to a side port 30 and a filling tube 32 through a common flow line 34. Side port 30 is coupled to a side port outlet 31 and to spray assembly 110. As cup 22 is filled with a sample through filling tube 32, a valve 36 and the spray valves block the path to side port outlet 31 and spray assembly 110. However, when flow is directed through side port 30, a valve 38 blocks the path to filling tube 32.

As shown in FIG. 8, the piston lid 24 has an annular upper portion 60 that rests outside of the cup 22. Accordingly, the upper portion 60 of the lid 24 has an interior surface 62 and an exterior surface 64 such that the interior surface 62 helps to define a chamber 66 within lid 24. The press 20 has a tapered head 68, which enters the chamber 66 as press 20 moves down onto lid 24. An annular nut 70 positioned above the tapered head 68 engages a set of threads 72 on the exterior surface 64 of the upper portion 60 of the lid 24. Consequently, the hydraulic press 20 is operable to force the lid 24 down into cup 22.

The piston lid 24 has a lower portion 74, which rests inside the cup 22 when the lid 24 is in place. A wear ring 76 and a piston seal 78 are positioned between an outer surface 80 of the lower portion 74 of the lid 24 and an inside wall 82 of the cup 22. The bottom 84 of the lid 24 is tapered inwardly to facilitate downward movement into the cup 22.

Referring now to FIGS. 4 and 5, the spray assembly 110 is shown spraying a material sample onto a vertically-oriented test panel (shown in FIGS. 1 and 2) mounted on slide tray 94. The slide tray 94 comprises two perpendicular surfaces 96 and 98 that are joined such that slide tray 94 has an L-shaped cross-section. The programmable linear motion system 18 allows slide tray 94 to move laterally with respect to spray assembly 110 and hydraulic press assembly 12 to accommodate various spray tests. The path of travel of the slide tray 94 is governed by cylinder piston assembly 90.

Figure 6:
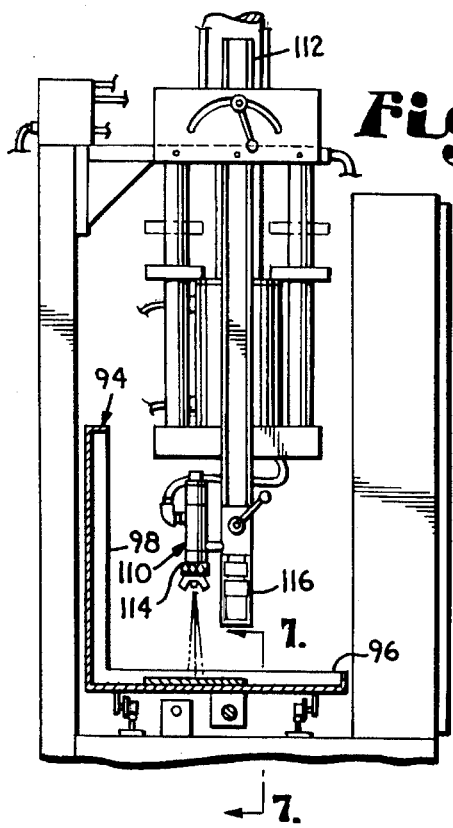
Figure 9:
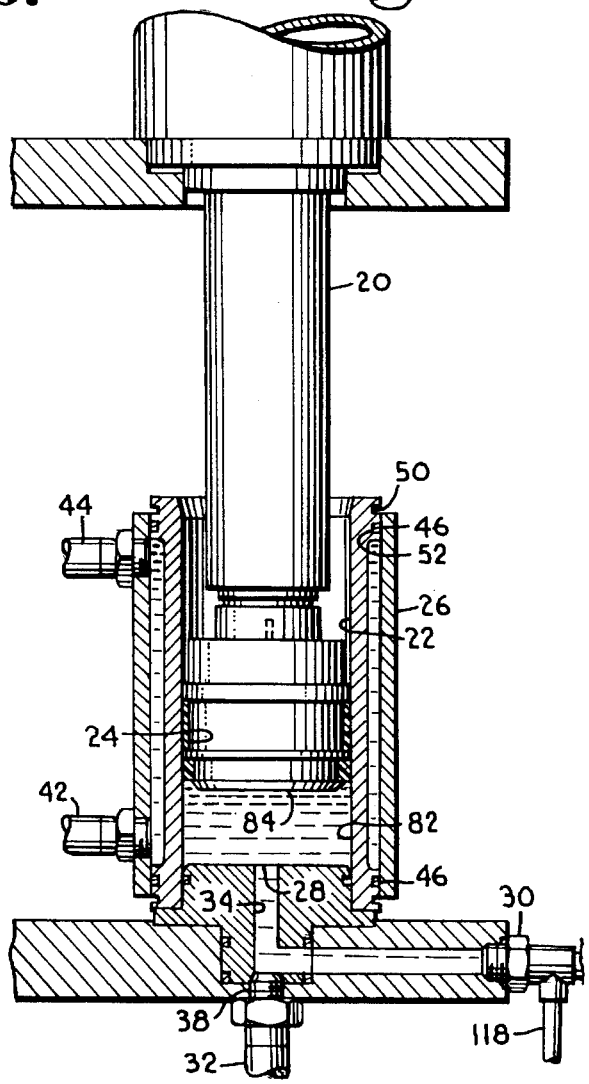
Figure 7:
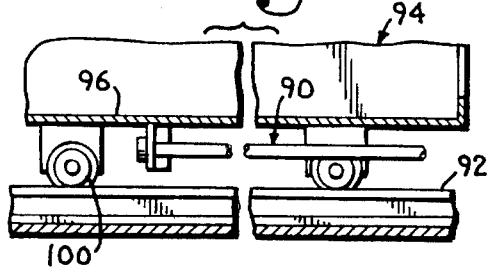

As shown in FIGS. 3 and 6, the slide tray 94 utilizes wheels 100 to move back and forth along tracks 92 located on either side of the cylinder piston assembly 90. The spray assembly 110 comprises a bracket 112 which may be moved to adjust the position of a spray valve 114 and a spray valve 116 to a variety of distances from the slide tray 94. In FIG. 3, bracket 112 is shown in two different positions so that spray valves 114 and 116 are positioned at two different distances from vertical surface 98 although the valves 114 and 116 remain perpendicular to surface 98 in both positions. By contrast, both the bracket 112 and spray valves 114 and 116 are perpendicular to horizontal surface 96 in FIG. 6. Thus, spray valves 114 and 116 and bracket 112 may be placed in a number of different positions with respect to surfaces 96 and 98.

Figure 10:
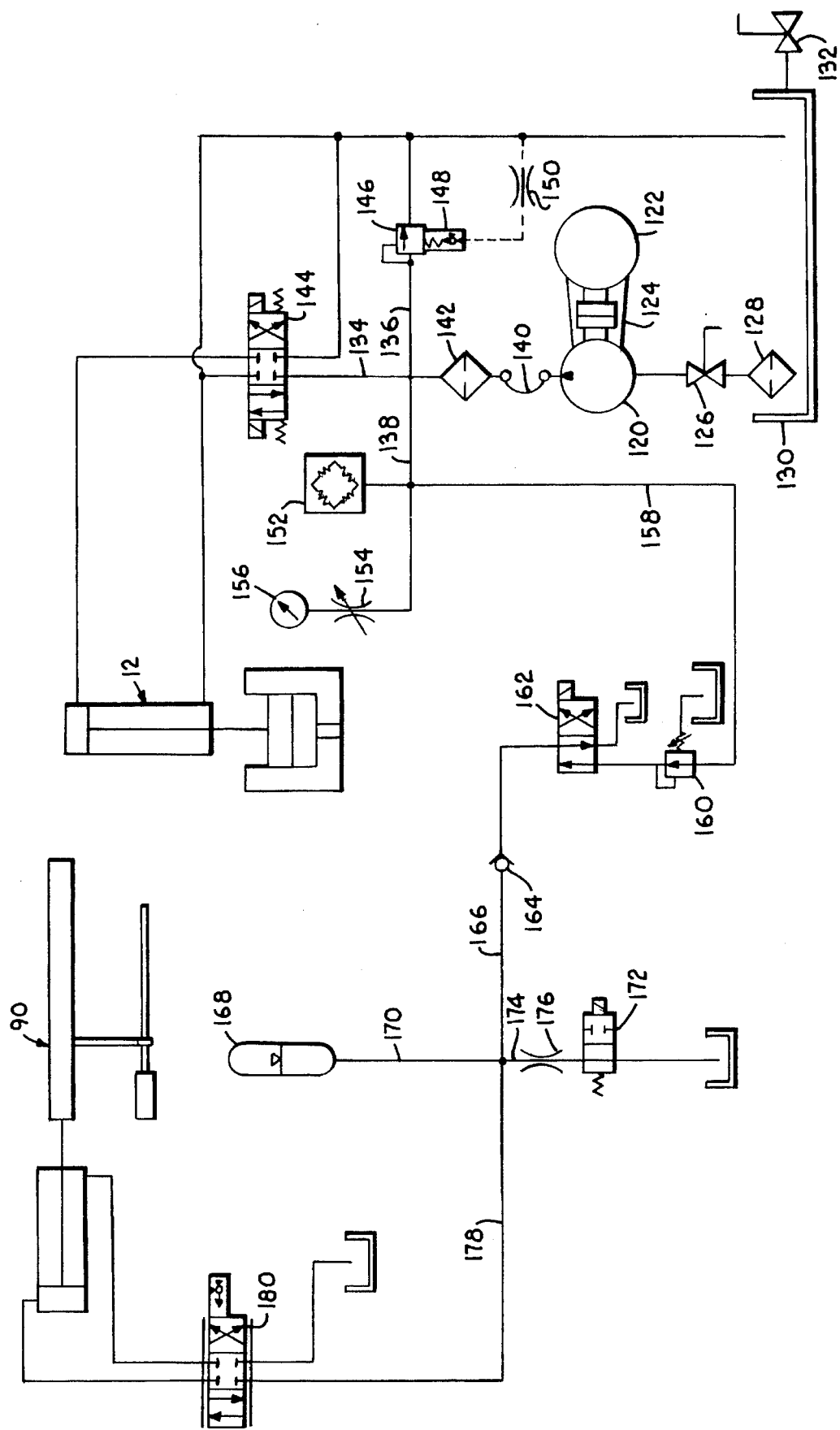

A schematic of the hydraulic system for the hydraulic press flow viscometer is shown in FIG. 10. A hydraulic pump 120 is coupled to an electric motor 122 through housing 124. A valve 126 and a strainer 128 couple pump 120 to a reservoir 130 and valve 132. Pump 120 is coupled to lines 134, 136 and 138 through a shaft coupling 140 and a filter 142. Line 134 is connected to a directional valve 144, which is coupled to hydraulic press assembly 12. Line 136 leads to a relief valve 146, a relief pilot 148 an orifice 150, and reservoir 130. Line 138 leads to a pressure transducer 152, a snubber 154 and a gauge 156, and line 158.

Line 158 leads to a valve 160, a directional valve 162, a check valve 164, and line 166. Further, line 166 is coupled to accumulator 168 by line 170 and coupled to accumulator valve 172 by line 174 and orifice 176. Finally, line 166 is coupled to cylinder piston assembly 90, which moves slide tray 94, by line 178, and a proportional valve 180.

In operation, the hydraulic press flow viscometer system 10 is capable of accurately measuring spray characteristics at various pressure, temperature and speed settings. Material pressure is maintained within one percent of the set point over the entire range from 500 to 4000 pounds per square inch ("psi"). The sample can be regulated within one degree of the desired temperature setting between 50° and 100° F. Further, robot speeds adjustable from 0 to 40 inches per second simulate robotic applications in assembly plants.

The temperature of the material is regulated by water chiller 40 shown in FIG. 1. Water chiller 40 circulates water at a desired temperature in proximity to the material to control the material temperature. In the present invention, the water chiller 40 is set to a desired temperature, typically between 50° and 100° F. The water then flows through a hose into inlet 42 of annular jacket 26 and circulates within the annular space between jacket 26 and sample storage cup 22. As more water enters the annular space, water exits the annular space through outlet 44 and is returned to chiller 40 for improved temperature control. The temperature of the sample inside cup 22 may be raised or lowered depending upon the temperature of the water circulating around cup 22. The time required to achieve the desired temperature will depend on a number of factors including the ambient temperature, the desired temperature, and the material being tested. When a temperature of 77° F. is desired, it has been found that a typical sample will reach this temperature within ten minutes. Thus, it is advisable to run chiller 40 for at least ten minutes before initiating the actual spray testing of the sample.

In a preferred embodiment, the water exiting the annular space through outlet 44 is directed through a manifold (not shown) before returning to chiller 40. The manifold allows for extended temperature control of the sample from the time it leaves cup 22 until it arrives at spray valve 114 or 116 by circulating water through tubes (not shown) inside the jacketed flow line 118 which also contains the material flow line. The manifold also provides a return line to chiller 40 to regulate water flow and water temperature.

The control pad 54 on control panel 14, shown in FIG. 1, allows an operator to specify several of the parameters for initiating a particular spray test. First, the Master On button is depressed so that system 10 is operable. Then, the Main Pressure control is set to the desired pressure for the material cup 22, typically between 500 and 4000 psi, and a digital readout of the selected pressure value is provided at display 56. In a preferred embodiment, the pressure reading is actually taken at the digital pressure transducer (shown in FIG. 10) because the system is designed such that the same pressure exists for the material in cup 22 and for the hydraulic fluid at the transducer. The most preferred embodiment of the present invention provides a 3:1 safety factor and includes one or more maximum pressure backups to assure that the pressure does not exceed 4000 psi. If the pressure were to exceed 4000 psi, the safety factor would be reduced below the desired level.

Further, the Fan/Bead control on control pad 54 may be set to specify whether the spray assembly 110 will spray the sample in a fan pattern or a bead pattern. Spray valve 114 is used to spray the fan pattern because it has an airless tip, and spray valve 116 is designated to spray the bead pattern because it has an air assist tip. If desired, the bead pattern can be made wider and flatter as the material is extruded by utilizing an air regulator (not shown) on valve 116. With a regulator, a number of air outlets are provided around the material orifice that alter the shape of the pattern based on the pressure set at the regulator. Of course, a variety of spray patterns may be achieved by providing the appropriate tips on valves 114 and 116. Depending on the pattern selected at pad 54, the programmable controller sends a signal to the solenoids which in turn drive open the appropriate air actuated spray valve 114 or 116. Spray valve 116 typically sprays a bead pattern up to two inches wide, and spray valve 114 typically sprays a fan pattern six to twelve inches wide.

Before testing, the filling tube 32 may be utilized to draw a material sample into cup 22. This is achieved by selecting the Pressurize Cylinder control on control pad 54 to lower press 20 to the bottom of cup 22. With the bottom of filling tube 32 in contact with a material sample and valve 36 closed, the Return control on pad 54 is selected to raise press 20 to provide suction for drawing the sample up through filling tube 32, common flow line 34, outlet 28 and into cup 22. However, since filling tube 32 is initially filled with air, a slug of air is drawn into cup 22. This slug of air must be purged from cup 22 because it will affect the test results. Therefore, after the air has been drawn into cup 22, press 20 is temporarily idled. Valve 38 then closes off filling tube 32, which is now primed with sample material. Next, valve 36 is opened to side port outlet 31, and press 20 is lowered to push the slug of air out of cup 22 through outlet 28, side port 30 and side port outlet 31. Often a small quantity of sample will also be purged through side port outlet 31. Upon closing valve 36 to side port outlet 31 and reopening valve 38 to filling tube 32, press 20 is again raised to draw the sample into cup 22.

Some materials are too thick to be drawn into cup 22 through filling tube 32, but these and other materials may be placed in cup 22 manually by removing and cleaning an empty cup and replacing it with a filled cup. To manually fill cup 22, press 20 is raised and clamp plates 88 and any other fasteners holding cup 22 in place may be removed. Clamp plates 88 are split shot clamps each mounted on a post 86 and held in place by Allen screws (not shown). When the screws are loosened, plates 88 slide up their respective posts 86 and out of the way. Then, jacket 26 is disconnected and cup 22 may be pulled out. Piston lid 24 slides out of cup 22 for convenient cleaning and filling. After cup 22 is replaced by repositioning clamp plates 88, O-rings 46 and other fasteners, press 20 is lowered until it contacts piston lid 24 so that annular nut 70 may be conveniently engaged with threads 72.

Once cup 22 is filled with a material sample and secured within assembly 12, the desired spray test begins with press 20 moving down into cup 22 causing the piston lid 24 to purge the sample from cup 22 toward the spray assembly 110. The piston lid 24 effectively cleans the inside of cup 22 by scraping any material off the inside wall 82 as it descends. After the material has been spray tested, cup 22 is ready to be refilled with another material sample.

In a preferred embodiment of the present invention, the material sample may be sprayed in the direction of a test panel attached to horizontal surface 96 and/or vertical surface 98 of slide tray 94. Spraying the sample onto a vertical test panel is particularly advantageous in performing sag tests, which tests determine the amount of material that may be applied before it begins to sag. Alternatively, the test panel may be placed at an angle with respect to surface 96 and/or surface 98. Additionally, spray assembly 110 may be manipulated to vary the angle or distance at which the sample travels to reach the target. In a preferred embodiment, bracket 112 can be adjusted so that the distance from the tip of valve 114 or 116 to the test panel (or target) is variable up to a maximum distance of 16 inches. FIG. 3 illustrates the mobility of bracket 112. Similarly, spray valves 114 and 116 may be pointed in different directions with respect to bracket 112. Spray valves 114 and 116 are shown perpendicular to bracket 112 in FIG. 2, parallel to bracket 112 in FIG. 6, and at acute and obtuse angles with respect to bracket 112 in FIG. 3. Consequently, spray valves 114 and 116 may be directed to a test panel on slide tray 94 at a number of angles and distances. Alternatively, spray valves 114 or 116 may be directed toward a material recovery cup to test the spray delivery rate.

A particular spray test may be controlled by either interface 58, which determines the movement of the slide tray 94, or by a specified spray time if movement of the slide tray 94 is not desired. Therefore, if movement of the slide tray 94 is the desired means of controlling the test, the Slide On/Off control is set to Slide On and various test parameters are programmed into the interface 58. Otherwise, a specified spray time may govern the testing by setting the Slide On/Off control to Slide Off, setting the Spray Time control to the desired spray time, which is digitally displayed at the display 56 adjacent to the control pad 54, and depressing the Spray Start control. Many commercially available timers can operate the Spray Time control, and the preferred embodiment utilizes an Omron H3BA Timer.

The programmable controller operates slide tray 94 in response to the input of spray test parameters at interface 58. For example, the velocity of the slide tray 94 may be set between one inch per second and forty inches per second. The tray velocity may vary considerably from test to test, but the return velocity (as the tray returns to its starting position), though adjustable, may be conveniently defaulted at 10 inches per second. Further, the linear positions at which spraying will start and stop may also be programmed through interface 58. Accurate measurement of the speed and position of slide tray 94 may be accomplished by a positional transducer such as the Temposionics TTS-RBU0420DE004. In a preferred embodiment of the present invention, the full stroke of slide tray 94 is 41 inches, but the present invention could be readily adapted to provide a linear motion system having a shorter or longer stroke. Slide tray 94 can also be programmed to travel a distance less than a full stroke by selecting a shorter reach position. Finally, the number of times slide tray 94 repeats its path of travel for spray testing is also selected at interface 58.

As an example, a spray test might be conducted where slide tray 94 will travel through its full stroke (e.g. 41 inches) at 20 inches per second, but spray testing will commence at 10 inches and discontinue at 35 inches. Then, slide tray 94 will return to its starting position at a rate of 10 inches per second before repeating the same spray test two more times. All of the above-mentioned parameters are programmed into the controller through interface 58 and may be easily adjusted. For instance, a virtually identical spray test may be conducted by reducing the reach position from 41 inches to 37 inches and increasing the return velocity from 10 inches per second to 15 inches per second.

When using a hydraulic system for spray testing, it is important to avoid varying the pressure of the material sample. For example, if the system has only a single hydraulic pump and both the slide tray cylinder piston assembly 90 and the hydraulic press assembly 12 are being pressurized at the same time, the material pressure may vary somewhat and have an adverse effect on test results. Therefore, such a system should either have two separate pumps, one two-chamber pump, or a single pump with an accumulator.

As shown in FIG. 10, a preferred embodiment of the present invention provides an accumulator 168 for assembly 90 to improve the pressure stability of the material sample. More specifically, accumulator 168 powers slide tray 94 as it starts down the track, then it charges during the return cycle of slide tray 94. In this way, assembly 12 and assembly 90 are not being pressurized at the same time.

Electric motor 122 drives hydraulic pump 120, which pumps hydraulic fluid stored in reservoir 130 throughout the hydraulic system. Assembly 90 and accumulator 168 are separated from pump 120 by lines 158 and by valves 160, 162 and 164.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

We claim:

1. A system for spray testing a material sample with a hydraulic press flow viscometer that extrudes high viscosity materials at high pressures, said system comprising:

a container for holding a material sample, said container having an outlet through which said material sample may be discharged;

hydraulic press means, adapted to be coupled with said container, for compressing the material sample within the container and expelling the sample from the container through said outlet;

means for regulating the temperature and pressure of the sample within the container; and a spray assembly adapted to be coupled with said container outlet for directing the expelled sample material in a spray action at a target so that spray delivery rate, spray pattern width and/or sag characteristics of the sample material may be measured.

2. The system of claim 1, wherein the target is a material recovery cup.

3. The system of claim 1, wherein the target is a test panel coupled to a slide tray.

4. The system of claim 3, further comprising means for controlling the movement of the slide tray.

5. The system of claim 4, wherein said means for controlling comprises means for coordinating the movement of the slide tray with the spray action of said spray assembly.

6. The system of claim 1, wherein said means for regulating temperature comprises a jacket surrounding said container to define a fluid circulation space between said jacket and said container.

7. The system of claim 6, wherein said means for regulating temperature comprises means for circulating a fluid to affect the temperature of the material within said container.

8. The system of claim 1, further comprising means for regulating the temperature of the expelled sample.

9. The system of claim 8, wherein said means for regulating the temperature of the expelled sample comprises a jacketed flow line.

10. The system of claim 1, further comprising means for filling said container with a material sample.

11. The system of claim 10, wherein said means for filling comprises a filling tube.

12. The system of claim 1, wherein the spray action is a fan pattern.

13. The system of claim 1, wherein the spray action is a bead pattern.

14. A method of spray testing a material sample using a hydraulic press flow viscometer that extrudes high viscosity materials at high pressures in a hydraulic spray testing system, said method comprising the steps of:

providing a sample of the material in a container having a lid;

regulating the temperature and pressure of the material sample at desired levels;

forcing the lid of the sample storage container downwardly into the container; and spraying the sample onto a test surface so that spray pattern width and/or sag characteristics of the material sample may be measured.

15. The method of claim 14, said method further comprising the step of measuring the spray pattern width of the sample on the test surface.

16. A method of spray testing a material sample using a hydraulic spray testing system, wherein the amount of material sample used during spray testing is minimized, said method comprising the steps of:

providing a sample of the material in a sample storage container having a lid;

regulating the temperature and pressure of the material sample at desired levels;

forcing the lid of the sample storage container downwardly into the container using hydraulic press; and spraying the sample into a material recovery cup so that spray delivery rate into the material recovery cup may be measured.

17. The method of claim 16, said method further comprising the step of determining the spray delivery rate by dividing the mass of the recovered material by the delivery time.

18. A method of spray testing a material sample using a hydraulic press flow viscometer that extrudes high viscosity materials at high pressures in a hydraulic spray testing system, said method comprising the steps of:

providing a sample of the material in a container;

pumping the material sample out of the container and into a spray valve assembly at a preselected pressure; and spraying the material sample onto a moving test panel to simulate a robotic application so that spray pattern width and/or sag characteristics of the material sample may be measured.

* * * * *